United States Patent
Jin et al.

(10) Patent No.: US 9,580,441 B2
(45) Date of Patent: Feb. 28, 2017

(54) DENTAL COMPOSITIONS BASED ON POLYMERIZABLE RESINS CONTAINING ISOSORBIDE

(71) Applicants: Xiaoming Jin, Middletown, DE (US); Bernard Koltisko, Milton, DE (US)

(72) Inventors: Xiaoming Jin, Middletown, DE (US); Bernard Koltisko, Milton, DE (US)

(73) Assignee: Dentsply International Inc., York, PA (US)

( * ) Notice: Subject to any disclaimer, the term of this patent is extended or adjusted under 35 U.S.C. 154(b) by 0 days.

(21) Appl. No.: 14/156,927

(22) Filed: Jan. 16, 2014

(65) Prior Publication Data

US 2014/0200288 A1    Jul. 17, 2014

Related U.S. Application Data

(60) Provisional application No. 61/753,109, filed on Jan. 16, 2013.

(51) Int. Cl.
*A61K 6/083* (2006.01)
*C07D 493/04* (2006.01)

(52) U.S. Cl.
CPC .......... *C07D 493/04* (2013.01); *A61K 6/083* (2013.01)

(58) Field of Classification Search
CPC .................................................. A61K 6/083
See application file for complete search history.

(56) References Cited

U.S. PATENT DOCUMENTS

2004/0266941 A1* 12/2004 Houston et al. .............. 524/506

FOREIGN PATENT DOCUMENTS

WO    WO 9613511 A1 *  5/1996  ............ C07H 13/12

* cited by examiner

*Primary Examiner* — Michael Pepitone
(74) *Attorney, Agent, or Firm* — Leana Levin; Douglas J. Hura; David A. Zdurne

(57) ABSTRACT

Disclosed herein are polymerizable dental materials and dental products based upon such materials. More particularly, disclosed are materials and products based upon BPA-free, polymerizable resins that are derived from 1,4:3,6-dianhydro-glucidol (isosorbide).

3 Claims, No Drawings

DENTAL COMPOSITIONS BASED ON POLYMERIZABLE RESINS CONTAINING ISOSORBIDE

RELATED PATENT APPLICATION

This application claims priority to U.S. Provisional Patent Application No. 61/753,109, filed Jan. 16, 2013.

TECHNICAL FIELD

Disclosed herein are polymerizable dental materials and dental products based upon such materials. More particularly, disclosed are materials and products based upon BPA-free, polymerizable resins that are derived from 1,4:3,6-dianhydro-glucidol (isosorbide), which comes from renewable sources such as corn.

BACKGROUND

Dental materials such as for example, dental filling materials, often include liquid polymerizable organic monomers and/or polymers, reactive diluents, polymerization initiators, stabilizers, and fillers. Such composite materials have their good mechanical properties such as high flexural strengths, high compressive strengths and hardness. Further, they are often polishable and readily accept suitable dyes. The most frequently used monomers are esters of methacrylates and higher multifunctional alcohols or isocyanates such as the bismethacrylate of biphenol-A diglycidyl ether, urethane bismethacrylates. Aromatic dials are often used to make polymerizable resins having good thermal and mechanical stability.

Bisphenol A (BPA) has been widely used in the manufacture of plastics and is present in many products, including dental products. Both the U.S. Food and Drug Administration and the National Toxicology Program at the National Institute of Health have expressed concern about the potential health effects associated with BPA.

Although BPA is not an ingredient in any dental products, it has been detected in some of the degraded dental products that contain BPA-based dental resins. BisGMA is one such BPA-based dental resin and has been widely used in many dental products. Regardless of the debate over the effect of potentially leached BPA from cured dental products that contain BisGMA or its derivatives, there are increasing efforts to manufacture BPA-free resins.

BisGMA is a high viscosity, dimethacrylate resin. Various structural modifications on BisGMA have been made in order to reduce its viscosity and to minimize the polymerization shrinkage and curing stress. The rigid aromatic moiety in BisGMA does contribute well to the high strength in cured BisGMA and its derivatives, although they are usually accompanied by higher shrinkage and higher curing stress. Conventional aliphatic resins, such as TEGDMA or UDMA are flexible and have low viscosity but they usually offer lower mechanical property. A variety of cyclic aliphatic moieties were also incorporated into polymerizable resins and an improved chemical property was demonstrated due to the rigid nature. However, most of monomer resins containing cyclic moiety are highly crystalline due to its chain regularity, which would limit its application as matrix resin for formulated dental composites. Therefore oligomeric resins have to be prepared, but these amorphous resins tend to have higher viscosity. Accordingly there is reduced cross-linking density after curing and furthermore lower mechanical property would result.

Bisphenol A (BPA) in particular is one such aromatic diol that has been widely used in epoxy resin, modified methacrylate resin, polyethersulfone/ketone, polyester, polycarbonate and the like, for use in dental materials. Resins or polymers from fully aliphatic diols are less popular due to their relative lower thermal stability. However, there have been investigations of resins and polymers based on cyclic aliphatic compounds, especially those that are multi-cyclic. Interest in such cyclic aliphatic dials has increased due to potential concerns of some aromatic diol, especially BPA. Accordingly, BPA-free resins or polymers would be highly desirable if they possessed the same or comparable thermal and mechanical stabilities as the BPA counterparts.

SUMMARY

It was theorized that by incorporating a cyclic aliphatic moiety into polymerizable resin that a rigid BPA-free polymerizable resin with balanced overall performance could be achieved.

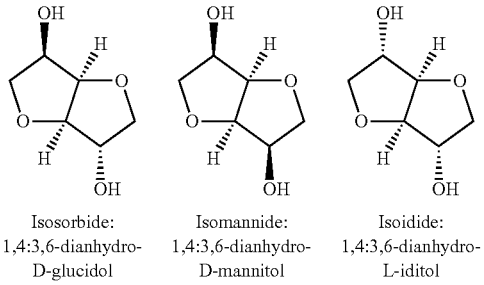

Isosorbide:
1,4:3,6-dianhydro-
D-glucidol

Isomannide:
1,4:3,6-dianhydro-
D-mannitol

Isoidide:
1,4:3,6-dianhydro-
L-iditol

As one isomer of 1,4:3,6-dianhydro-hexitol (see above), the 1,4:3,6-dianhydro-glucidol(Isosorbide) is particularly of interest for its potential use in formulated dental products such as restoratives and the like. It is expected that such a moiety would provide an improved optical, thermal and mechanical properties in comparison to linear aliphatic analogies. Like TMCD, Isosorbide has been used in many polyesters or polycarbonates and is known to be a co-monomer. Some of key features from such polymers are high impact resistance, optical clarity, thermal stability and biodegradability in addition to being BPA-free.

During investigations, TMCD was used in BPA-free polymerizable resins and an effectively optimized resin composition/process for TMCD-based urethane resin had been developed, from which polymerizable resin with high TMCD-content and lower viscosity resulted. However, though its overall mechanical property is better than UDMA resin, the mechanical properties remain lower than those of BisGMA-based resin systems. Therefore, suitable monomers to serve as components for BPA-free polymerizable resins are still desired. Isosorbide caught our attention because polymer grade isosorbide recently become commercially available, and is similar to TMCD in structure since both of them are a bicyclic diol, which would offer high heat-resistance and high Tg due to the rigid nature.

Scheme: representative isosorbide-based urethane resin

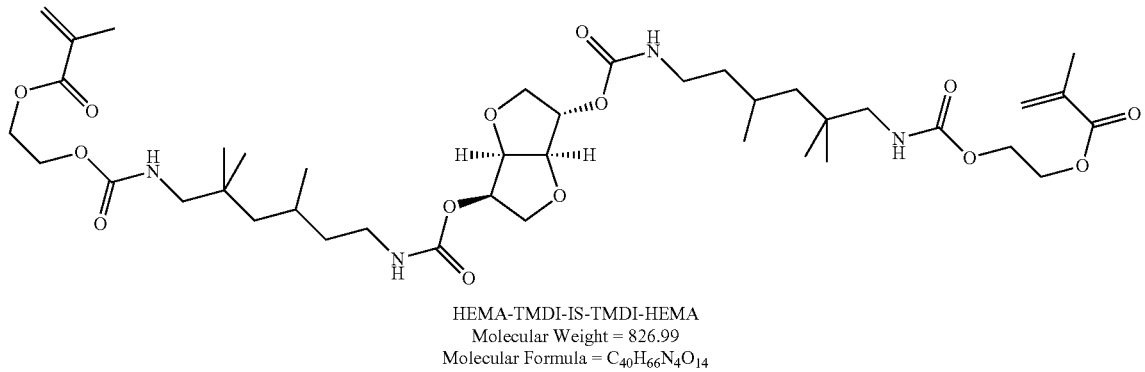

HEMA-TMDI-IS-TMDI-HEMA
Molecular Weight = 826.99
Molecular Formula = $C_{40}H_{66}N_4O_{14}$

DETAILED DESCRIPTION

As stated above dental restorative materials, such as composites, adhesives, and cements have traditionally contained derivatives of BPA as the base polymeric component. These include monomers such as Bis-GMA, Bis-DMA, EPADMA and BADGE. There are also many examples of urethane resins produced by combining BPA and BPA derivatives with di-isocyanates. These components have provided exceptional properties such as high durability, chemical resistance and optical properties to formulated dental products.

Due to potential health concerns over human exposure to BPA, many producers of polymers which contain BPA and derivatives of BPA have been seeking new chemistry approaches. For instance, TMCD has been shown to be an effective substitute for BPA in polyester resin systems.

Disclosed herein, isosorbide is used as a building block for the development of new dental resin systems. The resultant isosorbide derivatives are substituted for their BPA derivative analogues in restorative formulations. The result is that high performance dental restorative materials are made free of BPA containing materials.

It is therefore, an accomplishment of the present disclosure to provide the use of isosorbide based monomers used in dental formulations, including restorative composites, bonding agents, cements, luting agents, bases, and liners.

Isosorbide monomers with one or more pendant vinyl groups, such as, but not limited to methacrylic or acrylic moieties are also provided according to the present disclosure. These compounds may also include groups such as ethylene oxide or propylene oxide in their composition.

The isosorbide monomers used herein may have one or more pendant epoxy groups. Urethane derivatives may be provided, normally produced through reaction of isosorbide with isocyanate based compounds. Isosorbide derivatives with phosphate, and other ionic functionalities, and isosorbide derivatives which may contain combinations of functionalities are provided. Resins or macromonomers which may incorporate isosorbide in its structure and dental formulations with isosorbide based compounds are within the scope of the present disclosure.

Therefore, according to the present disclosure, a dental material is provided based upon an isosorbide polymerizable resin. An example of such a dental product is a dental restorative that is light curable, such that it is placed into a prepared dental cavity and then exposed to electromagnetic radiation of an appropriate wavelength to initiate (or co-initiate if other initiators are useful) to polymerize the material. Before polymerization, the material must have suitable flow properties to allow it to be placed into the prepared cavity, yet may also be required to have a certain stiffness or resistance to flow to allow the dental practitioner the ability to manipulate it. Further, after polymerization, wear, toughness, fracture resistance, and other thermal and mechanical stabilities must be of a certain, desirable nature. While such aspects of dental restoratives are well developed with respect to BPA dental materials, it has been unexpected that such properties could be achieved by isosorbide materials.

Isosorbide is a diol molecule and it should be readily reacted with other condensation monomers to build up linkages such as ester, carbonate, urethane and the like (see Scheme 1) and to form polymerizable resins accordingly. Additional examples of isosorbide-based polymerizable resins are given in Scheme 2 through 8. For example, if isosorbide reacts with an isocyanate, it would yield a urethane-based resin; if isosorbide reacts with a carboxylic monomer, then it would yield an ester type of resin. The physical and mechanical properties of the resulting isosorbide-based resins would vary depending upon the resin's linkages, detailed molecular structures and the pathways to make such resins.

In Table I and II, examples are given for typical isosorbide-based polymerizable resins as illustrated by Scheme 1. In addition, such typical reaction pathways towards different types of polymerizable resin based on isosorbide are also given in Scheme 2-7. The resulting resins ranged from semicrystalline to low viscosity liquid or higher viscosity liquids, depending upon the resin compositions. These resins can be further formulated with any other resin and conventional initiators to make it polymerizable. Thus, clear, rigid cured resin can be resulted after it is formulated with different photoinitiators, such as CQ/EDAB or CQ/LTPO.

In Scheme 2, the reaction pathway towards urethane trimer resin based on isosorbide is illustrated. This resulting trimer resin is semi-crystalline with a melting point of 125° C. This resin can be formulated with other resins and conventional initiators to make it polymerizable. Thus, clear, rigid cured resin can be achieved after it is formulated with different photoinitiators, such as CQ/EDAB or CQ/LTPO and exposed to visible light.

In Scheme 3, the reaction pathway towards urethane type of polymerizable resin based on isosorbide from isosorbide/TMDI/HEMA in the presence of TEGDMA is illustrated. This resulting urethane resin is liquid resin but with very high viscosity. This resin can be formulated with other resins and conventional initiators to make it polymerizable. Thus, clear, rigid cured resin can be achieved after it is formulated with different photoinitiators, such as CQ/EDAB or CQ/LTPO and exposed to visible light.

In Scheme 4, the reaction pathway towards urethane type of polymerizable resin based on isosorbide from isosorbide/TMDI/HPMA in the presence of TEGDMA is illustrated. This resulting urethane resin is liquid resin but with very high viscosity. This resin can be formulated with other resins and conventional initiators to make it polymerizable. Thus, clear, rigid cured resin can be achieved after it is formulated with different photoinitiators, such as CQ/EDAB or CQ/LTPO and exposed to visible light.

In Scheme 5, another reaction pathway towards urethane type of polymerizable resin based on isosorbide from isosorbide/IPDI/HEMA in the presence of TEGDMA is illustrated. This resulting urethane resin is liquid resin with high isosorbide content but very low viscosity. This resin can be formulated with other resins and conventional initiators to make it polymerizable. Thus, clear, rigid cured resin can be achieved after it is formulated with different photoinitiators, such as CQ/EDAB or CQ/LTPO and exposed to visible light.

In Scheme 6-7, the reaction pathway towards carbonate trimer type of polymerizable resin based on isosorbide from CDI/Isosorbide/HEMA or CDI/Isosorbide/AMAHP via a solution process is illustrated. This resulting carbonate resin is a liquid resin with low viscosity. This resin can be formulated with other resins and conventional initiators to make it polymerizable. Thus, clear, rigid cured resin can be achieved after it is formulated with different photoinitiators, such as CQ/EDAB or CQ/LTPO and exposed to visible light.

(1)

Scheme 1: General Illustration of Isosorbide-based Polymerizable Resins

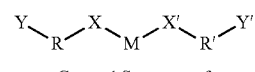

General Structure of Isosorbide-based Resins (2)

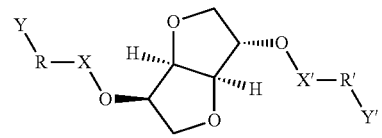

Resin Structure based on Isosorbide

M: Isosorbide moiety
X or X': same or different carbonate, ester, urethane, ether linkage
R or R': same or different alkyl, alicyclic, aromatic residues or substitutes aromatic residues etc;
Y or Y': same or different polymerizable groups such as vinyl, vinylether, acrylic, methacrylic, epoxide, etc Scheme 2: Synthetic Pathway to Polymerizable Urethane Trimer of Isosorbide

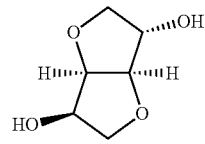

Isosorbide
Molecular Weight = 146.14
Molecular Formula = $C_6H_{10}O_4$

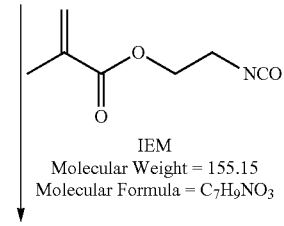

IEM
Molecular Weight = 155.15
Molecular Formula = $C_7H_9NO_3$

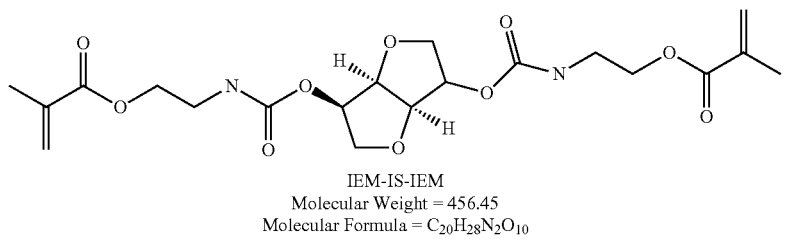

IEM-IS-IEM
Molecular Weight = 456.45
Molecular Formula = $C_{20}H_{28}N_2O_{10}$ Scheme 3: Synthetic Pathway to Polymerizable Urethane Oligomer of Isosorbide
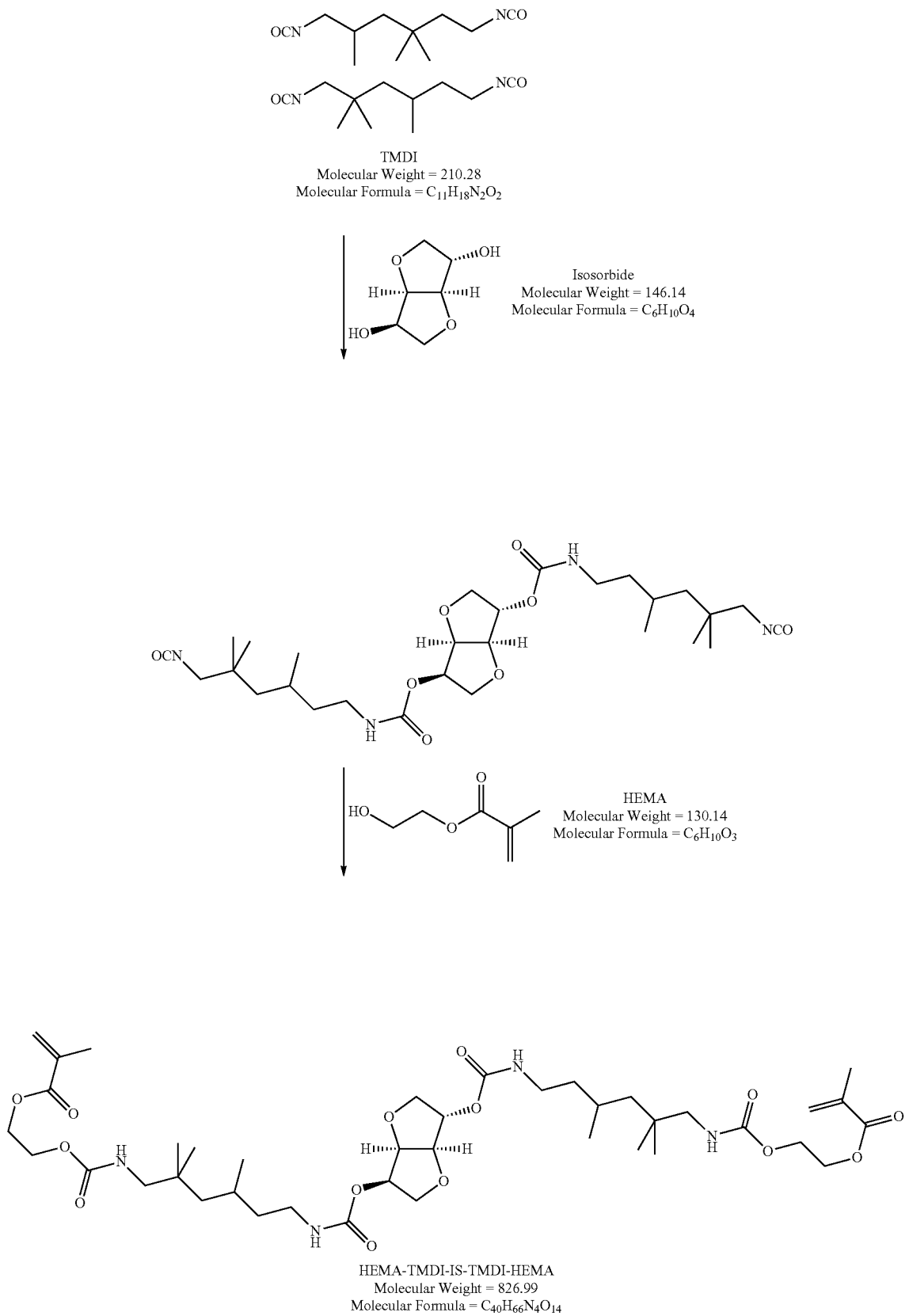

Scheme 4: Synthetic Pathway to Polymerizable Urethane Oligomer of Isosorbide
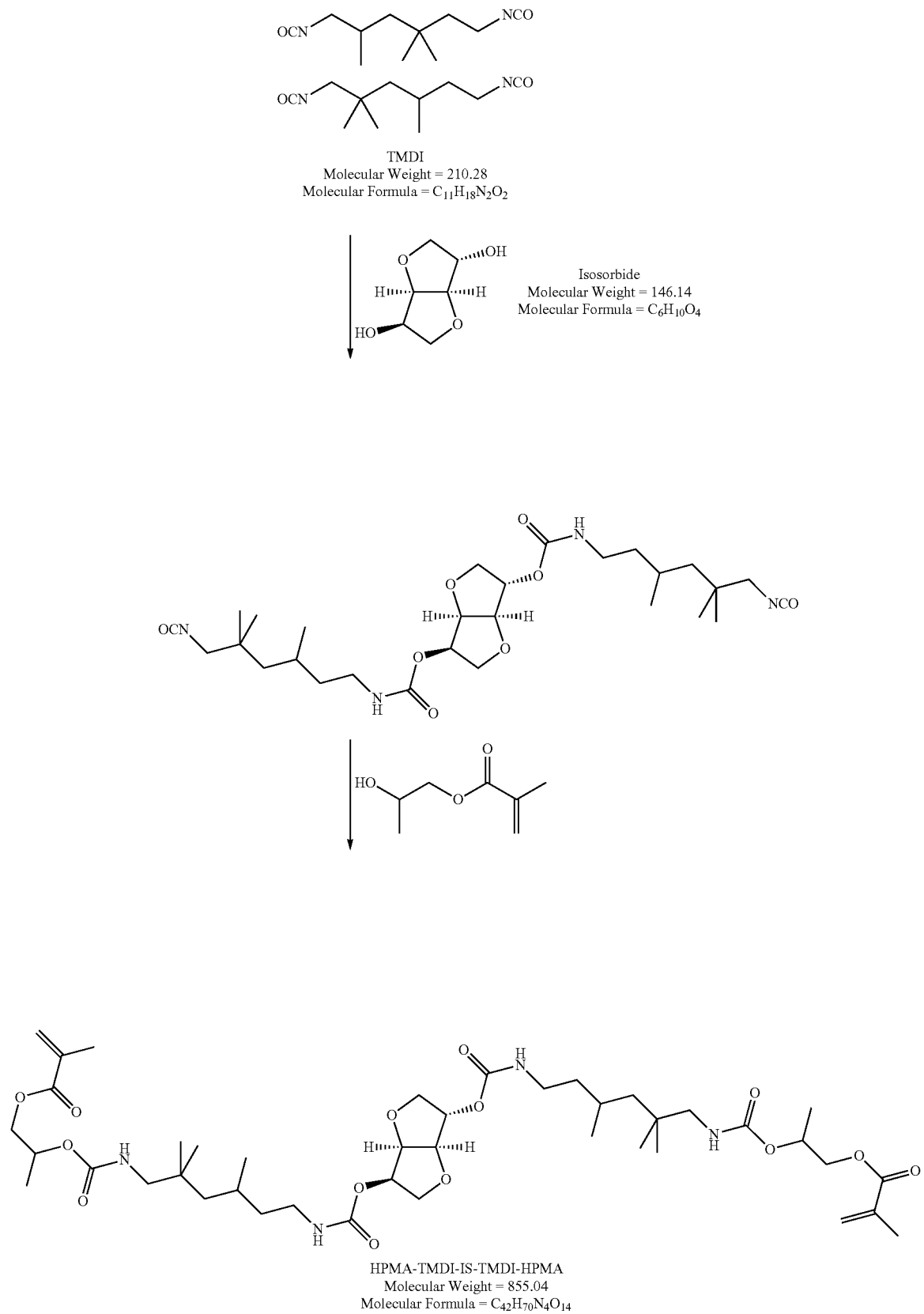

Scheme 5: Synthetic Pathway to Polymerizable Urethane Oligomer of Isosorbide
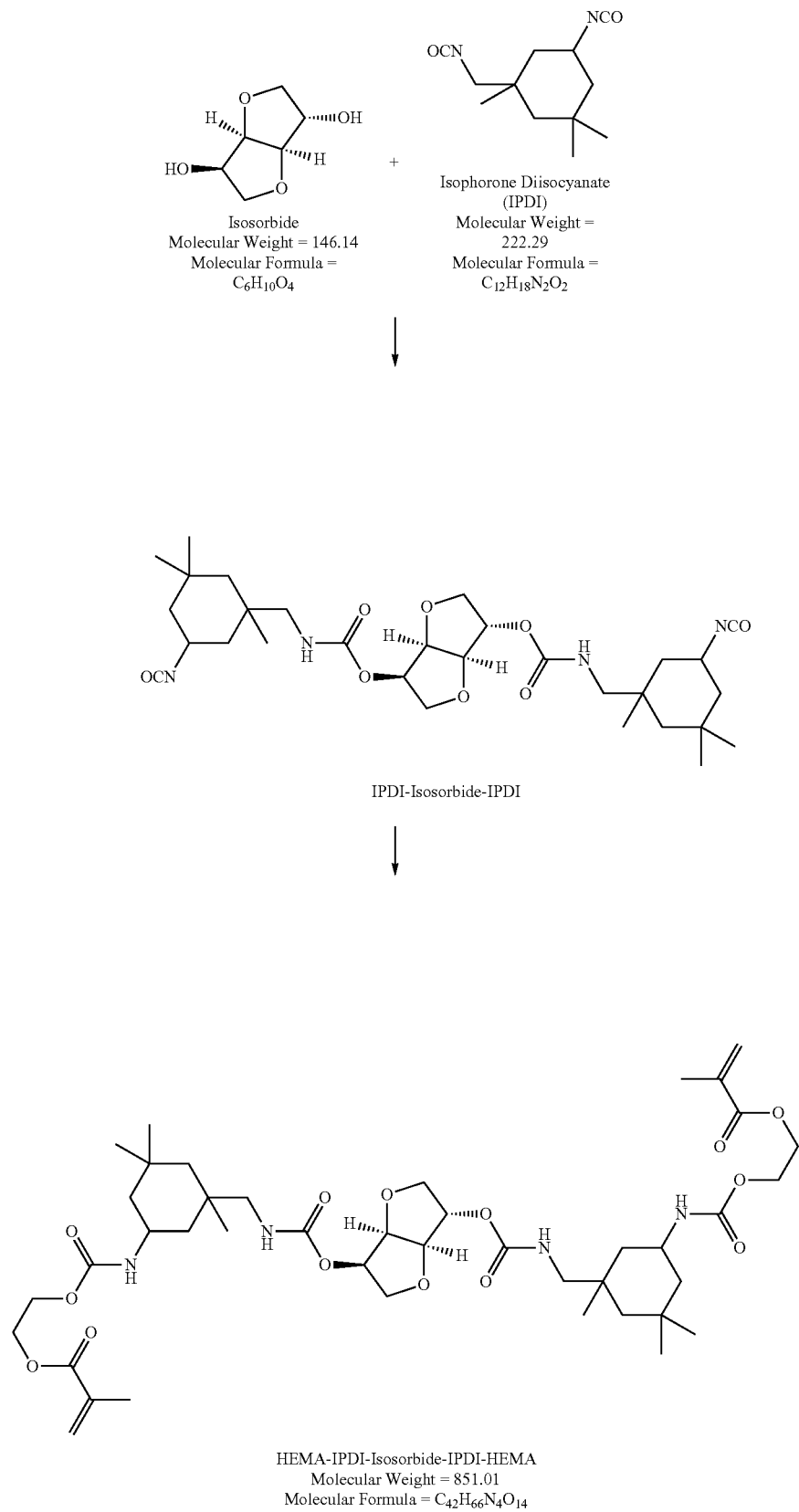
HEMA-IPDI-Isosorbide-IPDI-HEMA
Molecular Weight = 851.01
Molecular Formula = $C_{42}H_{66}N_4O_{14}$ Scheme 6: Synthetic Pathway to Polymerizable Carbonate Trimer of Isosorbide

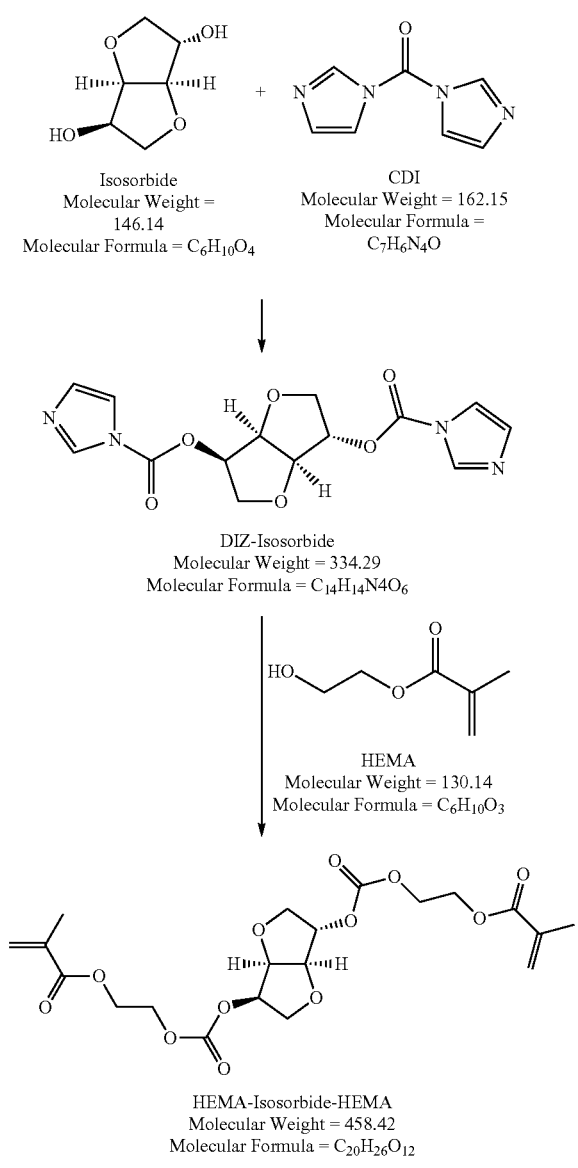

Scheme 7: Synthetic Pathway to Polymerizable Carbonate Trimer of Isosorbide

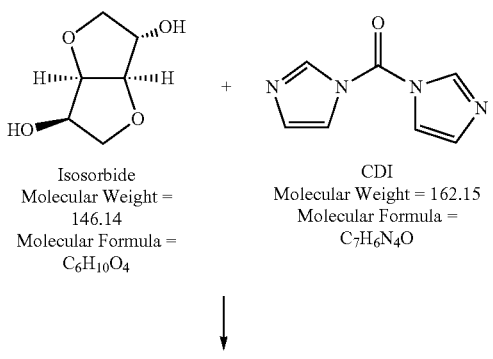

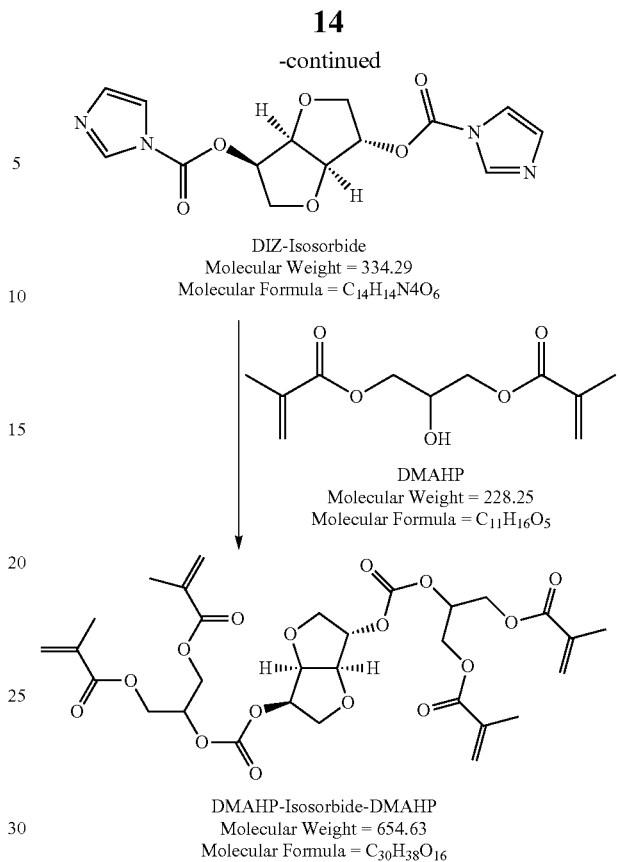

The polymerizable isosorbide-based composition according to the present disclosure may include a filler, stabilizer, polymerization initiator or cure package, or the like. Fillers may be inorganic filler and/or organic filler. In embodiments, fillers suitable for use in dental compositions in accordance with the present disclosure include quartz, glass ceramic or glass powders, as well as aluminium- and silicon oxide powder, in particular silicate glasses, Ba/Al silicate glasses and barium glasses as well as mixtures thereof. Other inorganic powders such as $La_2O_3$, $ZrO_2$, $BiPO_4$, $CaWO_4$, $BaWO_4$, $SrF_2$, $Bi_2O_3$, and/or organic fillers, such as polymer granulate or a combination of organic/or inorganic fillers could are also suitable filler materials. The filler are used as powders with a particle size of from about 0.010 micron to about 50 micron.

Total filler loading should vary from about 1% to about 95% by weight, depending upon the end applications. In Table II and III, examples of formulated isosorbide-based resin systems and their corresponding composites with about 40% of filler loading are shown. As can be seen from these Tables, extremely low curing stress can be achieved from the BPA-free resin systems formulated according to the present disclosure, though they offer only slightly lower shrinkage in comparison to a BPA-containing resin (for example, TPH resin, a urethane-modified BisGMA derivative).

An exemplary cement in accordance with a one embodiment of the present disclosure for dental and/or medical use includes from about 10 to about 30 percent by weight of an isosorbide monomer or co-monomer having at least one polymerizable group, from about 15 to about 35 percent by weight of a polymerizable monomer as diluent and a stabilizer, from about 50 to about 65 percent by weight of a filler and from about 0.34 to about 12 percent by weight of the polymerization initiator component(s).

A composite restorative composition in accordance with another embodiment of the present disclosure for dental and/or medical use includes from about 5 to about 25 percent by weight of an isosorbide monomer or co-monomer having at least one polymerizable group, from about 5 to about 20 percent by weight of a polymerizable monomer as diluent and a stabilizer, from about 50 to about 85 percent by weight of a filler and from about 0 to about 12 percent by weight of the polymerization initiator component(s).

A dental/medical sealer in accordance with one embodiment of the present disclosure for dental and/or medical use includes from about 15 to about 55 percent by weight of an isosorbide monomer or co-monomer having at least one polymerizable group, from about 20 to about 40 percent by weight of a polymerizable monomer as diluent and a stabilizer and from about 10 to about 50 percent by weight of a filler and 0.34 to about 12 percent by weight of the polymerization initiator component(s).

Test Methods:

NMR Analysis: 300 MHz NMR (Varian) was used to elusive the molecular structure and to monitor the reaction processing.

Photo DSC: DSC 2529 with photocaltometer (TA Instrument) was used to evaluate the photolysis and photopolymerization for the neat resin and/or any formulated resin system. Under both air and nitrogen, the test was performed. The light outputs and light spectrum can be tuned by using build-in filter, or additional UV filter or intensity-reducing filter.

Flexural strength and modulus are tested according to ISO 4049, 2×2×25 mm specimens were cured by three overlapped spot curing with Spectrum 800 with 13 mm light guide at 800 mw/cm$^2$, 20" for each spot on one side only. The cured specimens (6-10) were placed in DI water and stored at 37° C. for 24 hrs, then were sanded prior to the test at room temperature.

Compressive strength and modulus are tested according to ISO 9917, which is actually for water-based cements since ISO 4049 does not specify for compressive strength. ϕ4×6 mm glass slave as mold for specimen preparation (6). It was cured by Spectrum 800 at 800 mw/cm$^2$ from both top and bottom, at 20" each. The cured specimens (6-10) were placed in DI water and stored at 37° C. for 24 hrs, and then were sanded prior to the test at room temperature.

Polymerization Shrinkage was calculated from the density change before and after curing, which were measured by helium pycnometer (Micromeritics, AccuPyc II 1340) at 25.0° C. New in-house shrinkage test protocol was followed in this test: 3 pieces of round disc samples from a ϕ10×2 mm Teflon mold. It was presses between Mylar films and cured by Spectrum 800 at 800 mw/cm$^2$ for 20 seconds from top and bottom sides, respectively. The cured specimen is stored at room temperature for 2-3 hrs or for 24 hrs prior to the density measurement.

Shrinkage Stress was measured by using NIST/ADA's tensometer. Specimen with 2.25 mm in thickness (c-factor as 1.33) is cured for 60 seconds by DENTSPLY/Cauk's QHL light at 550 mw/cm2. The total stress at the 60$^{th}$ minute is taken to rank different materials.

EXAMPLES

Example 1

Synthesis of Isosorbide-Based Carbonate Resin

A carbobate-based dimethacrylate resin (XJ7-191 in Table I) was prepared by a two-step condensation reaction from Isosorbide and CDI in methylene dichloride under a dry air atmosphere at room temperature, then AMAHP was added along with potassium carbonate and tetrabutyl ammnium bromide into the system for additional couple of hours. After extraction to remove the catalysts and imidazole, additional diluent of TEGDMA was mixed in and the final liquid resin with higher viscosity of 430 Pa·s@20° C. could be achieved after removal of the solvent.

Example 2

Synthesis of Isosorbide-Based Carbonate Resin
(Scheme 6)

Isosorbide carbonate dimethacrylate trimer (XJ7-205 in Table I) was prepared by a two-step condensation reaction from Isosorbide and CDI in methylene dichloride under a dry air atmosphere at room temperature, then HEMA was added along with potassium carbonate and tetrabutyl ammnium bromide into the system for additional couple of hours. After extraction to remove the catalysts and imidazole, low viscosity liquid resin of 10 Pa·s@20° C. could be achieved after removal of the solvent.

Example 3

Synthesis of Isosorbide-Based Urethane Resin
(Scheme 2)

A urethane dimethacrylate trimer (XJ8-4 in Table I) was prepared by a one-step condensation reaction from Isosorbide and 2-isocyanateethyl methacrylate (IEM). The reaction was carried out in the presence of dibutyltin dilaurate in methylene dicloride under a dry air atmosphere at 30-35° C. for 4 h. After solvent was removed, semicrystallime resin could be achieved with $T_m$ of 125° C.

Example 4

Synthesis of Isosorbide-Based Urethane Resin

A urethane dimethacrylate oligomer (XJ7-189 in Table I) was prepared by a one-step condensation reaction from a preformed monohydroxy-monmethacrylate (ICEM, derived from TMDI and HPMA) and Isosorbide in the presence of dibutyltin dilaurate under a dry air atmosphere at 30-35° C. for 14 h. High viscosity liquid resin of 2180 Pa·s@20° C. was achieved.

Example 5/6

Synthesis of Isosorbide-Based Urethane Resin
(Scheme 3)

Urethane dimethacrylate oligomers (XJ8-19/XJ8-69 in Table I) were prepared by a two-step condensation reaction from isosorbide and slight excess of TMDI in presence of a diluent such as TEG DMA, followed by a reaction between the NCO-terminated prepolymer and 2-hydroxyethyl methacrylate (HEMA). The first reaction was carried out in the presence of dibutyltin dilaurate under a dry air atmosphere at 30-35° C. for 4 h. To the resulting prepolymer, BHT was added as inhibitor. TEGDMA can be used as inert diluent for ease of the reaction process. Liquid resin with moderate viscosity of 270-280 Pa·s@20° C. was achieved.

Example 7

Synthesis of Isosorbide-Based Urethane Resin
(Scheme 4)

Urethane dimethacrylate oligomers (XJ8-72 in Table I) were prepared by a two-step condensation reaction from isosorbide and slight excess of TMDI in presence of a diluent such as TEGDMA, followed by a reaction between the NCO-terminated prepolymer and 2-hydroxypropyl methacrylate(HPMA). The first reaction was carried out in the presence of dibutyltin dilaurate under a dry air atmosphere at 30-35° C. for 4 h. To the resulting prepolymer, BHT was added as inhibitor. TEGDMA can be used as inert diluent for ease of the reaction process. Liquid resin with higher viscosity of 550 Pa·s@20° C. was achieved.

Example 8

Synthesis of Isosorbide-Based Urethane Resin
(Scheme 5)

Urethane dimethacrylate oligomers (XJ8-78 in Table I) were prepared by a two-step condensation reaction from isosorbide and slight excess of IPDI in presence of a diluent such as TEGDMA, followed by a reaction between the NCO-terminated prepolymer and 2-hydroxyethyl methacrylate(HEMA). The first reaction was carried out in the presence of dibutyltin dilaurate under a dry air atmosphere at 30-35° C. for 4 h. To the resulting prepolymer, BHT was added as inhibitor. TEGDMA can be used as inert diluent for ease of the reaction process. Liquid resin with high viscosity of 1310 Pa·s@20° C. was achieved.

Example 9

Synthesis of Isosorbide-Based Urethane Resin

Urethane dimethacrylate oligomers (XJ8-11 in Table I) were prepared by a two-step condensation reaction from isosorbide and slight excess of TMDI in presence of a diluent such as HMDMA, followed by a reaction between the NCO-terminated prepolymer and 2-hydroxyethyl methacrylate (HEMA). The first reaction was carried out in the presence of dibutyltin dilaurate under a dry air atmosphere at 30-35° C. for 4 h. To the resulting prepolymer, BHT was added as inhibitor. TEGDMA can be used as inert diluent for ease of the reaction process. Liquid resin with high viscosity of 270 Pa·s@20° C. was achieved.

In Table II, Examples 8 through 15 showed further formulated resin compositions, which were comprised of Isosorbide-based polymerizable resins previously described, and other conventional (meth)acrylate resins and a variety of photoinitaitors (CO., LTPO etc). A comparable example 1 was also included with the exclusion of any Isosorbide-based resins disclosed herein.

Examples 16 through 23 showed those formulated composite compositions, which are comprised of a variety of formulated isosorbide-based polymerizable resins as described herein, and 40-82% wt/wt of glass filler mixtures. A comparable example 2 is also included with the exclusion of any isosorbide-based resins disclosed herein.

TABLE Ia

Resin Composition and Viscosity (at 20° C./500 Pa)

| Resins | Diol (grams) | Isocyanate or CDI (grams) | Hydroxylated Mathacrylate (grams) | Diluents (grams) | Viscosity at 20° C./500 Pa (Pa · s) |
|---|---|---|---|---|---|
| Control Example 1 | TMCD 25 | TMDI 81 | HEMA 60 | TEGDMA 30 | 80 |
| Control Example 2 | TMCD 25 | IPDI 85 | HEMA 60 | TEGDMA 30 | 1010 |
| Sample 1 (XJ7-191) | Isosorbide 37 | CDI 82 | AMAHP 110 | TEGDMA 19 | 430 |
| Example 2 (XJ7-205) | Isosorbide 37 | CDI 81 | HEMA 66 | | 10 |
| Example 3 (XJ8-4) | Isosorbide 74 | IEM 155 | | | crystalline Tm = 125° C. |
| Example 4 (XJ8-189) | Isosorbide 40 | ICEM 275 | | | 2180 |
| Example 5 (XJ8-19) | Isosorbide 40 | TMDI 127 | HEMA 91 | TEGDMA 45 | 270 |
| Example 6 (XJ8-69) | Isosorbide 73 | TMDI 231 | HEMA 165 | TEGDMA 85 | 280 |
| Example 7 (XJ8-72) | Isosorbide 73 | TMDI 231 | HPMA 183 | TEGDMA 85 | 550 |
| Example 8 (XJ8-78) | Isosorbide 73 | IPDI 245 | HEMA 165 | TEGDMA 185 | 1310 |
| Example 9 (XJ8-82) | Isosorbide 73 | TMDI 231 | HEMA 165 | TEGDMA 85 | 250 |
| Example 10 (XJ8-86) | Isosorbide 73 | TMDI 231 | HEMA 165 | TEGDMA 85 | 290 |
| Example 11 (XJ8-90) | Isosorbide 73 | TMDI 231 | HEMA 165 | HMDMA 81 | 270 |
| Example 12 (EBR10220) | Isosorbide 658 | TMDI 2083 | HEMA 1488 | TEGDMA 766 | 240 |
| Example 13 (EBR10224) | Isosorbide 658 | TMDI 2083 | HEMA 1488 | TEGDMA 766 | 260 |

TABLE II a: Composition Examples for Various Isosorbide-based Polymerizable Resins

|  | Example 1 (XJ7-191) | Example 2 (XJ7-205) | Example 3 (XJ8-4) | Example 4 (XJ7-189) |
|---|---|---|---|---|
| Resin Composition | Isosorbide/AMAHP/TEGDMA | Isosorbide/HEMA | Isosobide/IEM | Isosobide/ICEM/HEMA |
| Isosorbide-based Resin, | 90 | 100 | 100 | 67 |
| TEGDMA, | 10 | 0 | 0 | 0 |
| UDMA, (wt/wt, %) | 0 | 0 | 0 | 33 |
| Resin Form | Liquid | Liquid | crystalline | Liquid |
| Viscosity @ 20° C. Pa · s | 430 | 10 | $T_m = 125°$ C. | 2180 |
| Solubility @ 37° C. in water | partially soluble | insoluble | insoluble | insoluble |
| Solubility @ 37° C. in water/ethanol (50:50, w/w %) | soluble | partially soluble | insoluble | insoluble | b: Composition Examples for Various Isosorbide-based Polymerizable Resins

|  | Example 5 (XJ8-19) | Example 6 (XJ8-69) | Example 7 (XJ8-72) | Example 8 (XJ8-78) |
|---|---|---|---|---|
| Resin Composition | TEGDMA/Isosorbide/TMDI/HEMA | TEGDMA/Isosorbide/TMDI/HEMA | TEGDMA/Isosorbide/TMDI/HPMA | TEGDMA/Isosorbide/IPDI/HEMA |
| Isosorbide-based Resin, | 74.8 | 74.5 | 74.7 | 63.7 |
| TEGDMA, | 15.0 | 15.4 | 14.8 | 27.7 |
| HEMA | 1.8 | 1.6 | 0 | 1.4 |
| HPMA | 0 | 0 | 1.8 | 0 |
| UDMA, (wt/wt, %) | 8.5 | 8.5 | 8.7 | 7.2 |
| Resin Form | Liquid | Liquid | Liquid | Liquid |
| Viscosity @ 20° C. Pa · s | 270 | 280 | 550 | 1310 |
| Solubility @ 37° C. in water | insoluble | insoluble | insoluble | insoluble |
| Solubility @ 37° C. in water/ethanol (50:50, w/w %) | insoluble | insoluble | insoluble | insoluble |

TABLE III a: Physical Property for Various Formulated Isosobide-based Resins

|  | Formulated Resin 1 (DP1-21) | Formulated Resin 2 (XJ7-196) | Formulated Resin 3 (XJ7-208) | Formulated Resin 4 (XJ8-22) | Formulated Resin 5 (XJ8-23) |
|---|---|---|---|---|---|
|  | 75% Example 4 25% TEGDMA | 80% Example 1 20% TEGDMA | 100% Example 2 | 92.5% Example 5 7.5% TEGDMA | 80% Example 5 10% TEGDMA 10% Example 3 |
|  | 0.165% CQ 0.30% EDAB 0.015% BHT | 0.165% CQ 0.30% EDAB 0.015% BHT | 0.165% CQ 0.30% EDAB 0.015% BHT | 0.165% Ca 0.30% EDAB 0.015% BHT | 0.165% CQ 0.30% EDAB 0.015% BHT |
| Viscosity @ 20° C. Pa · s | 8 | 12 | 10 | 66 | 53 |
| Stress @ 60 min MPa | 0.36 | 1.10 | 2.30 | 1.32 | 1.92 | b: Physical Property for Various Formulated Isosorbide-based Composites

|  | Composite 9 XJ8-24 | TMCD Composite 4 XJ7-132 |
|---|---|---|
| Resins | Formulated Isosobide Resin 4 (XJ8-22) | Formulated TMCD Resin 4 (XJ7-130) |
| Fillers (wt/wt) | DP1-64/ 40% | LB8-131 40% |
| Stress @ 60 min MPa | 1.15/1.80 | 0.91/NA |

TABLE III-continued

| | | |
|---|---|---|
| Compressive Yield St. (MPa) | 142 ± 2 | 116 ± 3 |
| Compressive Modulus (MPa) | 3900 ± 80 | 3220 ± 440 |
| Flexural St. (MPa) | 94 ± 6 | 91 ± 2 |
| Flexural Modulus (MPa | 2980 ± 200 | 2710 ± 240 |

TABLE IV a: Compositions and Physical Property for Various Formulated Resins

| | Example 14 DP2-76 | Example 15 DP2-77 | Example 16 DP2-78 | Example 17 DP2-149 |
|---|---|---|---|---|
| | Isosorbide Resin 90% XJ8-19 10% TEGDMA 0.165% CQ 0.30% EDAB 0.015% BHT | Isosorbide Resin 80% XJ8-65 20% TEGDMA 0.165% CQ 0.30% EDAB 0.015% BHT | Isosorbide Resin 80% XJ8-65 20% HEDMA 0.165% CQ 0.30% EDAB 0.015% BHT | Isosorbide Resin 90% XJ8-69 10% HEDMA 0.165% CQ 0.30% EDAB 0.015% BHT |
| Viscosity@20° C. Pa · s | 40 | 10 | 20 | 40 |
| Stress @ 60 min (Vis/UV-Vis), MPa | 1.40/1.80 | 2.1/2.60 | 1.90/2.30 | 1.72/1.80 |
| Compressive Yield St. (MPa) | 133 ± 6 | 130 ± 5 | 134 ± 2 | 136 ± 2 |
| Compressive Modulus (MPa) | 2300 ± 110 | 2320 ± 120 | 2430 ± 240 | 2270 ± 160 |
| Flexural St. (MPa) | 79 ± 4 | 80 ± 6 | 73 ± 1 | 76 ± 4 |
| Flexural Modulus (MPa | 2020 ± 50 | 2020 ± 230 | 1750 ± 50 | 1930 ± 200 | b: Compositions and Physical Property for Various Formulated Resins

| | Example 18 DP2-164 | Example 19 DP2-194 | Example 20 DP3-9 | Example 21 DP3-30 |
|---|---|---|---|---|
| | Isosorbide Resin 85% XJ8-78 15% TEGDMA 0.165% CQ 0.30% EDAB 0.015% BHT | Isosorbide Resin 90% XJ8-72 10% TEGDMA 0.165% CQ 0.30% EDAB 0.015% BHT | Isosorbide Resin 83% XJ8-78 17% TEGDMA 0.165% CQ 0.30% EDAB 0.015% BHT | Isosorbide Resin 90% XJ8-86 10% HEDMA 0.165% CQ 0.30% EDAB 0.015% BHT |
| Viscosity@20° C. Pa · s | 40 | 65 | 25 | 40 |
| Stress @ 60 min (Vis/UV-Vis), MPa | 2.20/2.63 | 1.30/1.60 | 1.40/1.80 | 1.35/1.85 |
| Compressive Yield St. (MPa) | 150 ± 9 | 116 ± 4 | 127 ± 4 | 124 ± 1 |
| Compressive Modulus (MPa) | 2860 ± 50 | 2480 ± 80 | 2600 ± 90 | 2610 ± 40 |
| Flexural St. (MPa) | 92 ± 7 | 81 ± 5 | 103 ± 3 | 83 ± 4 |
| Flexural Modulus (MPa | 2430 ± 250 | 2050 ± 280 | 2630 ± 150 | 2170 ± 120 |

TABLE V

Compositions and Physical Property for Various Formulated Resins

| | Example 18 DP2-106 Isosobide Resin 90% XJ8-19 10% TEGDMA 0.165% CQ 0.40% LTPO 0.015% BHT | Example 19 DP2-107 Isosobide Resin 85% XJ8-65 15% TEGDMA 0.165% CQ 0.40% LTPO 0.015% BHT | Example 20 DP2-150 Isosobide Resin 90% XJ8-69 10% TEGDMA 0.165% CQ 0.40% LTPO 0.015% BHT | Example 21 DP2-165 Isosobide Resin 85% XJ8-78 15% TEGDMA 0.165% CQ 0.40% LTPO 0.015% BHT | Example 22 DP3-10 Isosobide Resin 83% XJ8-78 17% TEGDMA 0.165% CQ 0.40% LTPO 0.015% BHT | Example 23 DP3-31 Isosobide Resin 85% XJ8-65 15% TEGDMA 0.165% CQ 0.40% LTPO 0.015% BHT |
|---|---|---|---|---|---|---|
| Viscosity@20° C. Pa · s | 40 | 40 | 40 | 40 | 25 | 40 |
| Stress @ 60 min (Vis/UV-Vis), MPa | 2.25/2.65 | 2.05/2.60 | 2.05/2.60 | 2.45/2.90 | 3.00/3.00 | 2.20/2.40 |
| Compressive Yield St. (MPa) | 133 ± 5 | 125 ± 8 | 136 ± 4 | 150 ± 4 | 131 ± 4 | 123 ± 1 |
| Compressive Modulus (MPa) | 2000 ± 300 | 2110 ± 400 | 2220 ± 410 | 2110 ± 400 | 2700 ± 80 | 2610 ± 80 |
| Flexural St. (MPa) | 101 ± 15 | 88 ± 7 | 90 ± 5 | 80 ± 9 | 131 ± 4 | 99 ± 6 |
| Flexural Modulus (MPa) | 2530 ± 200 | 2150 ± 300 | 2240 ± 60 | 2150 ± 300 | 2830 ± 100 | 2450 ± 170 |

TABLE VI a: Compositions and Properties for Various Resin Composite

| | Composite | | | |
|---|---|---|---|---|
| | Composite 10 DP2-24 | Composite 11 DP2-80 | Composite 12 DP2-82 | Composite 13 DP2-83 |
| Resins (wt/wt, %) | DP2-9 Isosobide Resin 90% XJ8-19 10% TEGDMA 0.165% CQ 0.30% EDAB 0.015% BHT | Example 14 DP2-76 Isosobide Resin 90% XJ8-19 10% TEGDMA 0.165% CQ 0.30% EDAB 0.015% BHT | Example 15 DP2-77 Isosobide Resin 80% XJ8-65 20% TEGDMA 0.165% CQ 0.30% EDAB 0.015% BHT | Example 16 DP2-78 Isosobide Resin 80% XJ8-65 20% HMDMA 0.165% CQ 0.30% EDAB 0.015% BHT |
| Fillers (wt/wk, %) | DP1-64 80.0 | DP1-64 80.2 | DP1-64 80.8 | DP1-64 80.8 |
| Stress @ 60 min (Vis/UV-Vis), MPa | 1.85/2.30 | 2.20/2.25 | 2.60/2.70 | 2.42/2.35 |
| Compressive St. (MPa) | 305 ± 15 | 294 ± 19 | 294 ± 12 | 322 ± 15 |
| Compressive Modulus (MPa) | 6040 ± 620 | 5985 ± 430 | 5990 ± 390 | 6200 ± 330 |
| Flexural St. (MPa) | 135 ± 8 | 122 ± 18 | 118 ± 10 | 102 ± 19 |
| Flexural Modulus(MPa | 10000 ± 830 | 10140 ± 1080 | 10280 ± 150 | 8810 ± 600 | b: Compositions and Properties for Various Resin Composite

| | Composite | | | |
|---|---|---|---|---|
| | Composite 14 DP2-151 | Composite 15 DP2-166 | Composite 16 DP2-196 | Composite 17 DP3-12 |
| Resins (wt/wt, %) | Example 14 DP2-149 Isosobide Resin 90% XJ8-19 10% TEGDMA 0.165% CQ 0.30% EDAB 0.015% BHT | Example 14 DP2-164 Isosobide Resin 85% XJB-78 15% TEGDMA 0.165% CQ 0.30% EDAB 0.015% BHT | Example 15 DP2-194 Isosobide Resin 90% XJ8-72 10% TEGDMA 0.165% CQ 0.30% EDAB 0.015% BHT | Example 16 DP3-9 Isosobide Resin 83% XJ8-78 17% HMDMA 0.165% CQ 0.30% EDAB 0.015% BHT |
| Fillers (wt/wt, %) | DP1-64 80.0 | DP1-64 80.0 | DP1-64 80.8 | DP3-11 80.2 |
| Stress @ 60 min (Vis/UV-Vis), MPa | 1.85/2.30 | 1.85/2.30 | 2.60/2.70 | 2.10/2.22 |
| Compressive St. (MPa) | 305 ± 15 | 305 ± 15 | 297 ± 15 | 310 ± 16 |
| Compressive Modulus (MPa) | 6040 ± 620 | 6040 ± 620 | 5400 ± 540 | 5500 ± 480 |
| Flexural St. (MPa) | 135 ± 8 | 100 ± 10 | 117 ± 10 | 91 ± 13 |
| Flexural Modulus(MPa | 10000 ± 830 | 10900 ± 500 | 9840 ± 860 | 11190 ± 650 | c: Compositions and Properties for Various Resin Composite

| Composite | Composite 18 DP3-28 | Composite 19 DP3-32 | Composite 20 DP3-35 | Composite 21 DP3-58 | Composite 22 DP3-60 |
|---|---|---|---|---|---|
| Resins (wt/wt, %) | Example 16 DP3-9 Isosobide Resin 83% XJ8-78 17% TEGDMA 0.165% CQ 0.30% EDAB 0.015% BHT | Example 21 DP3-30 Isosobide Resin 90% XJ8-86 10% TEGDMA 0.165% CQ 0.30% EDAB 0.015% BHT | Example 21 DP3-30 Isosobide Resin 90% XJ8-86 10% TEGDMA 0.165% CQ 0.30% EDAB 0.015% BHT | Example 21 DP3-30 Isosobide Resin 90% XJ8-86 10% HMDMA 0.165% CQ 0.30% EDAB 0.015% BHT | Example 21 DP3-30 Isosobide Resin 90% XJ8-86 10% HMDMA 0.165% CQ 0.30% EDAB 0.015% BHT |
| Fillers (wt/wt, %) | DP3-11 83.0 | DP3-11 83.0 | DP3-34 83.0 | DP3-11 65.0 | DP3-34 65.0 |
| Stress @ 60 min (Vis/UV-Vis), MPa | 2.02/2.12 | 2.02/2.12 | 2.20/2.50 | 1.83/2.15 | 1.56/2.10 |
| Compressive St. (MPa) | 305 ± 17 | 316 ± 24 | 310 ± 24 | 302 ± 14 | 291 ± 23 |
| Compressive Modulus (MPa) | 5860 ± 450 | 5730 ± 370 | 5430 ± 350 | 4630 ± 410 | 4140 ± 510 |
| Flexural St. (MPa) | 100 ± 10 | 138 ± 12 | 137 ± 10 | 119 ± 10 | 115 ± 7 |
| Flexural Modulus (MPa) | 11950 ± 470 | 10900 ± 630 | 11150 ± 640 | 5700 ± 420 | 5600 ± 40 |

TABLE VII a: Compositions and Properties for Various Resin Composite

| | Composite | | | | |
|---|---|---|---|---|---|
| | DP2-109 | DP2-110 | DP2-152 | DP2-167 | DP2-197 |
| | | | Resins (wt/wt, %) | | |
| | DP2-106 Isosorbide Resin 90% XJ8-19 10% TEGDMA 0.165% CQ 0.40% LTPO 0.015% BHT | DP2-107 Isosorbide Resin 85% XJ8-65 15% TEGDMA 0.165% CQ 0.40% LTPO 0.015% BHT | DP2-150 Isosorbide Resin 90% XJ8-69 10% TEGDMA 0.165% CQ 0.40% LTPO 0.015% BHT | DP2-165 Isosorbide Resin 85% XJ8-78 15% TEGDMA 0.165% CQ 0.40% LTPO 0.015% BHT | DP2-195 Isosorbide Resin 90% XJ8-72 10% TEGDMA 0.165% CQ 0.40% LTPO 0.015% BHT |
| Fillers | DP1-64 | DP1-64 | DP1-64 | DP1-64 | DP1-64 |
| (wt/wt, %) | 80.0 | 80.0 | 80.0 | 80.9 | 80.9 |
| Stress @ 60 min (Vis/UV-Vis), MPa | 2.05/2.22 | 2.05/2.20 | 2.25/2.40 | 2.28/2.32 | 1.95/2.15 |
| Compressive St. (MPa) | 272 ± 16 | 278 ± 23 | 333 ± 12 | 310 ± 7 | 300 ± 12 |
| Compressive Modulus (MPa) | 5910 ± 300 | 5700 ± 330 | 6050 ± 340 | 6140 ± 110 | 5570 ± 350 |
| Flexural St. (MPa) | 121 ± 17 | 114 ± 13 | 138 ± 10 | 121 ± 9 | 134 ± 9 |
| Flexural Modulus (MPa | 10870 ± 900 | 9690 ± 1280 | 10500 ± 740 | 12800 ± 900 | 11210 ± 830 | b: Compositions and Properties for Various Resin Composite

| | Composite | | | | | |
|---|---|---|---|---|---|---|
| | DP3-13 | DP3-29 | DP3-33 | DP3-36 | DP3-59 | DP3-61 |
| | | | Resins (wt/wt, %) | | | |
| | DP3-10 Isosorbide Resin 83% XJ8-78 17% TEGDMA 0.165% CQ 0.40% LTPO 0.015% BHT | DP3-10 Isosorbide Resin 83% XJ8-78 17% TEGDMA 0.165% CQ 0.40% LTPO 0.015% BHT | DP3-31 Isosorbide Resin 90% XJ8-86 10% TEGDMA 0.165% CQ 0.40% LTPO 0.015% BHT | DP3-31 Isosorbide Resin 90% XJ8-86 10% TEGDMA 0.165% CQ 0.40% LTPO 0.015% BHT | DP3-31 Isosorbide Resin 90% XJ8-86 10% TEGDMA 0.165% CQ 0.40% LTPO 0.015% BHT | DP3-31 Isosorbide Resin 90% XJ8-86 10% TEGDMA 0.165% CQ 0.40% LTPO 0.015% BHT |
| Fillers | DP3-11 | DP3-11 | DP3-11 | DP3-34 | DP3-11 | DP3-34 |
| (wt/wt, %) | 80.2 | 83.0 | 83.0 | 83.0 | 65.0 | 65.0 |
| Stress @ 60 min (Vis/UV-Vis), MPa | 2.12/2.41 | 2.10/2.10 | 2.22/2.25 | 1.90/2.50 | 2.10/2.38 | 2.10/2.50 |
| Compressive St. (MPa) | 303 ± 21 | 325 ± 20 | 298 ± 18 | 315 ± 14 | 289 ± 14 | 283 ± 10 |
| Compressive Modulus (MPa) | 5410 ± 310 | 6360 ± 420 | 5730 ± 720 | 5900 ± 420 | 4550 ± 510 | 4430 ± 380 |
| Flexural St. (MPa) | 102 ± 9 | 118 ± 11 | 153 ± 8 | 140 ± 12 | 130 ± 9 | 129 ± 7 |
| Flexural Modulus (MPa | 12400 ± 730 | 11980 ± 950 | 12700 ± 380 | 12330 ± 610 | 6550 ± 330 | 6700 ± 340 |

It will be appreciated that various of the above-disclosed and other features and functions, or alternatives thereof, may be desirably combined into many other different systems or applications. Also, various presently unforeseen or unanticipated alternatives, modifications, variations or improvements therein may be subsequently made by those skilled in the art, and are also intended to be encompassed by the following claims.

We claim:

1. A polymerizable dental material derived from 1,4:3,6-dianhydro-glucidol, wherein the dental material has a formula of

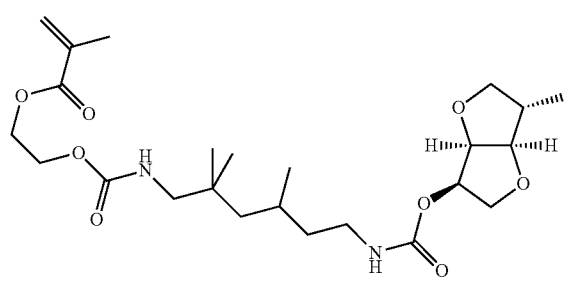

-continued

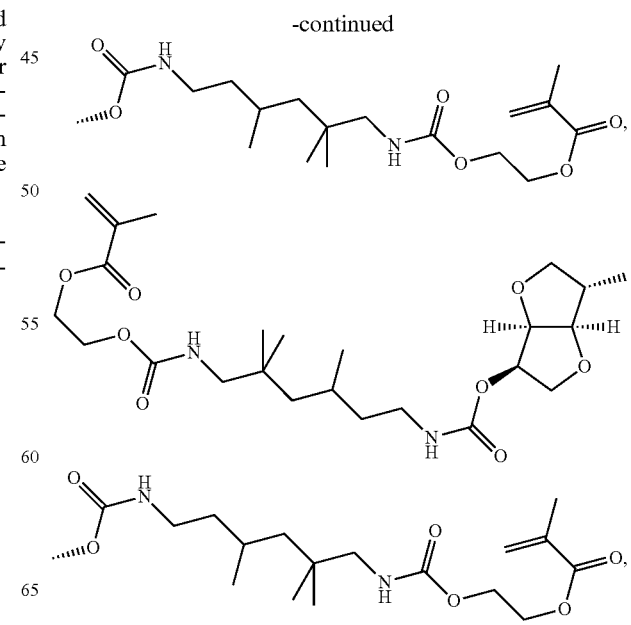

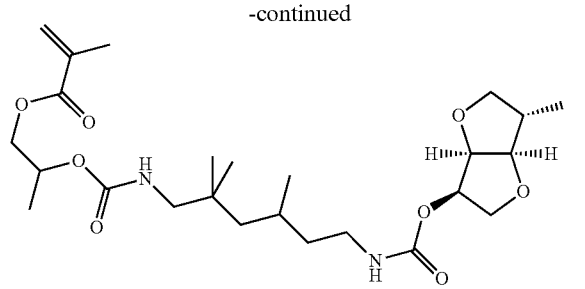
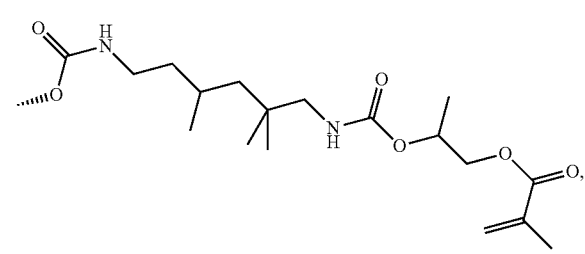
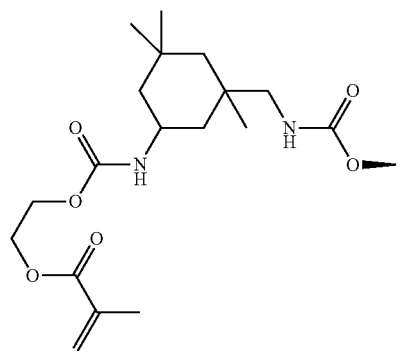
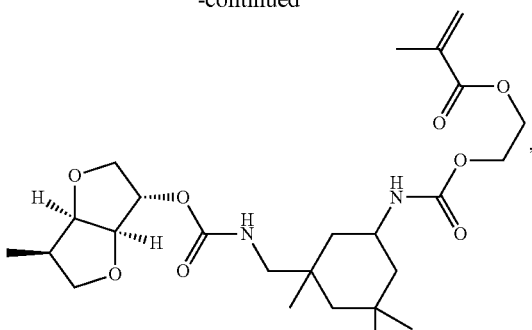
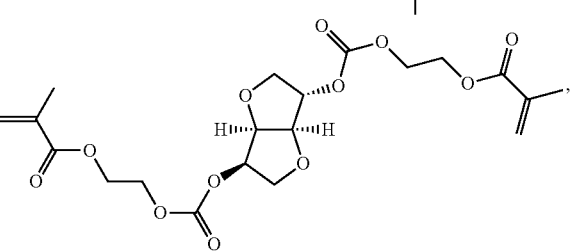
or
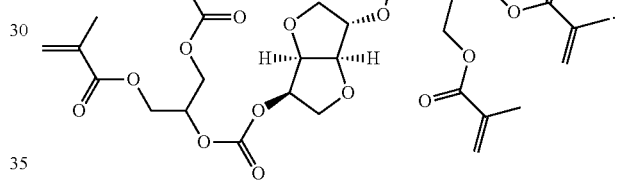
2. A dental composition comprising the dental material according to claim 1, a filler, a stabilizer, and a cure package.
3. A dental composition, comprising:
a monomer having a formula of
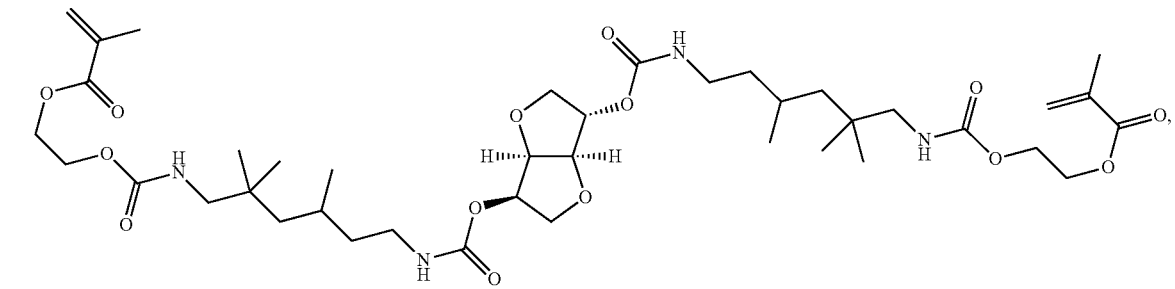
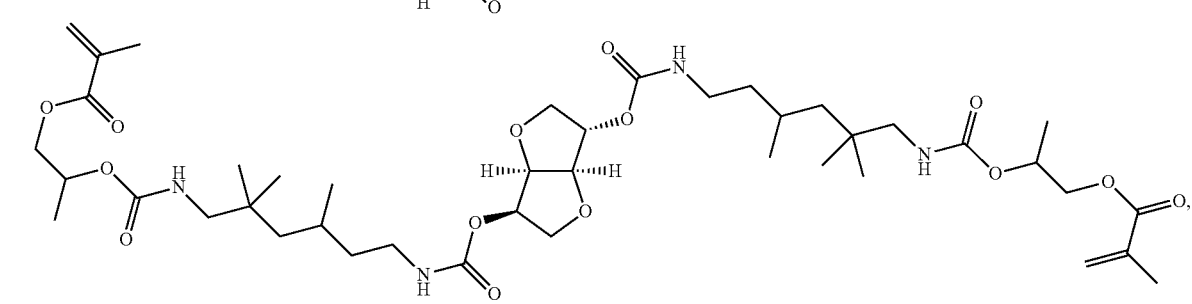

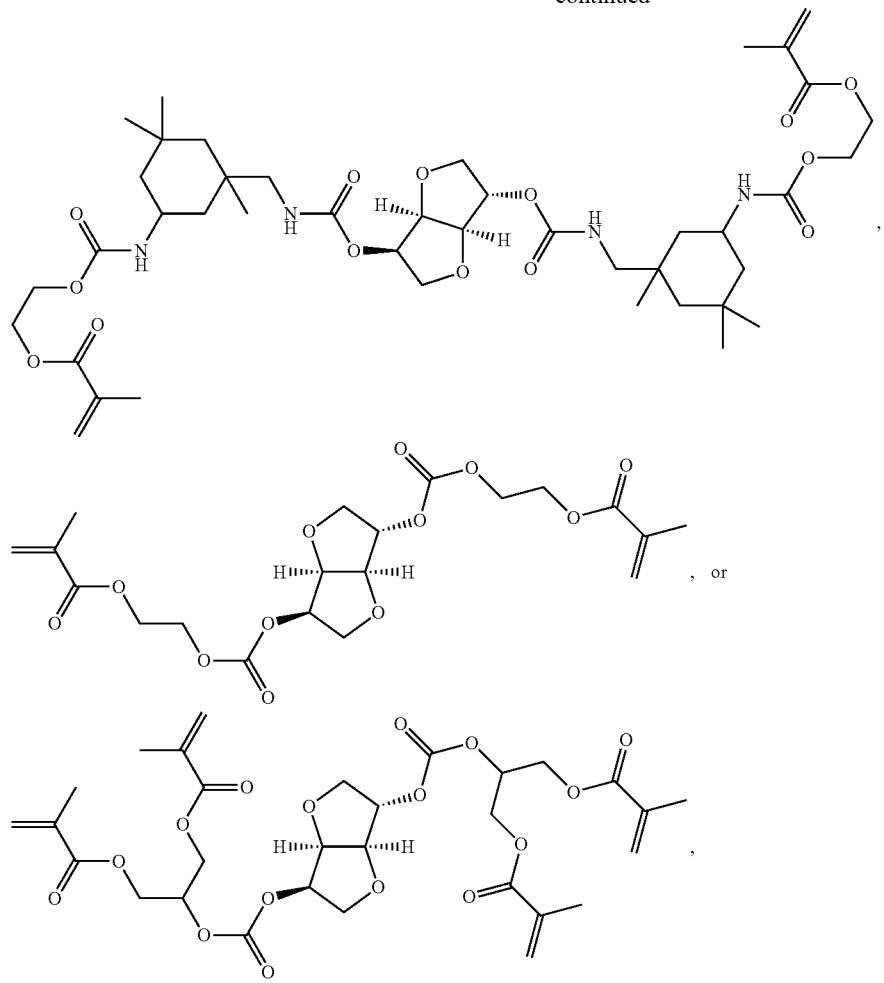
a polymerizable monomer,
a filler, and
at least one initiator.
* * * * *